US006458544B1

(12) United States Patent
Miller

(10) Patent No.: US 6,458,544 B1
(45) Date of Patent: Oct. 1, 2002

(54) METHODS FOR DETERMINING SINGLE NUCLEOTIDE VARIATIONS AND GENOTYPING

(75) Inventor: Andrew P. Miller, San Diego, CA (US)

(73) Assignee: DNA Sciences, Inc., Fremont, CA (US)

( * ) Notice: Subject to any disclaimer, the term of this patent is extended or adjusted under 35 U.S.C. 154(b) by 0 days.

(21) Appl. No.: 09/728,451

(22) Filed: Dec. 1, 2000

Related U.S. Application Data

(60) Provisional application No. 60/168,580, filed on Dec. 2, 1999.

(51) Int. Cl.[7] .............................. C12Q 1/68; C12P 19/34
(52) U.S. Cl. ......................................... 435/6; 435/91.1
(58) Field of Search .................................. 435/6, 91.1

(56) References Cited

U.S. PATENT DOCUMENTS

| | | |
|---|---|---|
| 4,656,127 A | 4/1987 | Mundy |
| 4,863,849 A | 9/1989 | Melamede |
| 4,865,968 A | 9/1989 | Orgel et al. |
| 4,962,037 A | 10/1990 | Jett et al. |
| 5,137,806 A | 8/1992 | LeMaistre et al. |
| 5,171,534 A | 12/1992 | Smith et al. |
| 5,210,015 A | 5/1993 | Gelfand et al. |
| 5,219,727 A | 6/1993 | Wang et al. |
| 5,302,509 A | 4/1994 | Cheeseman |
| 5,487,972 A | 1/1996 | Gelfand et al. |
| 5,518,900 A | 5/1996 | Nikiforov et al. |
| 5,538,848 A | 7/1996 | Livak et al. |
| 5,547,839 A | 8/1996 | Dower et al. |
| 5,639,611 A | 6/1997 | Wallace et al. |
| 5,654,419 A | 8/1997 | Mathies |
| 5,688,648 A | 11/1997 | Mathies |
| 5,707,804 A | 1/1998 | Mathies |
| 5,710,028 A | 1/1998 | Eyal et al. |
| 5,728,528 A | 3/1998 | Mathies et al. |
| 5,804,375 A | 9/1998 | Gelfand et al. |
| 5,821,058 A | 10/1998 | Smith et al. |
| 5,827,653 A | 10/1998 | Sammes et al. |
| 5,834,189 A | 11/1998 | Stevens et al. |
| 5,846,710 A | 12/1998 | Bajaj |
| 5,853,992 A | 12/1998 | Glazer et al. |
| 5,856,092 A | 1/1999 | Dale et al. |
| 5,863,736 A | 1/1999 | Haaland |
| 5,866,336 A | 2/1999 | Nazarenko et al. |
| 5,876,930 A | 3/1999 | Livak et al. |
| 5,885,775 A | 3/1999 | Haff et al. |
| 5,888,819 A | 3/1999 | Goelet et al. |
| 5,891,629 A | 4/1999 | Goldrick |
| 5,945,283 A | 8/1999 | Kwok et al. |
| 5,981,186 A | 11/1999 | Gabe et al. |
| 6,004,744 A | 12/1999 | Goelet et al. |
| 6,013,431 A | 1/2000 | Soderlund et al. |
| 6,020,137 A | 2/2000 | Lapidus et al. |
| 6,027,890 A | 2/2000 | Ness et al. |
| 6,107,061 A | 8/2000 | Johnson |
| 6,322,980 B1 * | 11/2001 | Singh ........................... 435/6 |

FOREIGN PATENT DOCUMENTS

| | | |
|---|---|---|
| EP | 0 229 943 | 7/1987 |
| EP | 0 601 889 | 6/1994 |
| EP | 0 412 883 | 11/1996 |
| GB | 2 252 407 | 8/1992 |
| GB | 2 317 951 A | 8/1998 |
| WO | WO 90/09455 | 8/1990 |
| WO | WO 90/13666 | 11/1990 |
| WO | WO 91/13075 | 9/1991 |
| WO | WO 92/15712 | 9/1992 |
| WO | WO 92/16657 | 10/1992 |
| WO | WO 93/05183 | 3/1993 |
| WO | WO 93/25563 | 12/1993 |
| WO | WO 97/22719 | 6/1997 |
| WO | WO 98/59066 | 12/1998 |

OTHER PUBLICATIONS

US 5,747,249, 05/1998, Smith et al. (withdrawn)

Ahern H.; Biochemical, reagent kits offer scientists good return on investment. The Scientist. Jul. 1995, vol. 9, No. 20, pp. 1–5.

Ausubel, F.M.; Polyacrylamide Gel Electrophoresis, Current Protocols in Molecular Biology; John Wiley & Sons; (1988); pp. 6.3–8, 6.36–6.38.

Litvak, Kenneth J.; Allelic discrimination using fluorogenic probes and the 5' nuclease assay. Genetic Analysis: Biomolecular Engineering. 1999, pp. 143–149.

Piggee, Christine A., Jochen Muth, Emanuel Carrilho, and Barry L. Karger; Capillary electrophoresis for the detection of known point mutations by single–nucleotide primer extension and laser–induced fluorescence detection. Journal of Chromatography A. 1997. pp. 367–375.

Singer, Maxine and Paul Berg; Genes & Genomes a Changing Perspective; University Science Books; 1991; p. 245.

Wu, Dan Y., Luis Ugozzoli, Bijay K. Pal and Bruce Wallace; Allele–specific enzymatic amplification of β–globin genomic DNA for diagnosis of sickle cell anemia; Proc, Natl. Acad. Sci USA; vol. 86.; Apr. 1989; pp. 2757–2760.

(List continued on next page.)

Primary Examiner—Kenneth R. Horlick
Assistant Examiner—Teresa Strzelecka
(74) Attorney, Agent, or Firm—Townsend and Townsend and Crew LLP

(57) ABSTRACT

The present invention provides methods and kits for determining the identity of a nucleotide at a variant site on a target nucleic acid. The methods begin with the template-dependent amplification of a target sequence under defined conditions to achieve selective incorporation of a nucleotide analog at the variant site. Amplification product is then subjected to limited degradation to create products having allele-specific sizes, which are subsequently separated on the basis of size. Finally, the number of products and their sizes is to assessed to determine the identity of the nucleotide(s) at the variant site and the genotype of the organism from which the target was obtained.

39 Claims, 4 Drawing Sheets

OTHER PUBLICATIONS

Ambrose, B. J. B. and Pless, R. C.; DNA Sequencing: Chemical Methods, *Methods in Enzymology*, (1987) vol. 152, pp. 522–539.

Brand, Eve et al., Structural Analysis and Evaluation Of The Aldosterone Synthase Gene In Hypertension, *Hypyertension*, (1998) vol. 32, pp. 198–204.

Cardullo, R. A. et al., Detection of Nucleic Acid Hybridization by Nonradiative Fluorescence Resonance Energy Transfer, *Proc. Natl. Acad. Sci. USA*, Dec. 1988, vol. 85, pp. 8790–8794.

Chen, Xiangning and Kwok; Pui–Yan; Homogeneous Genotyping Assays For Single Nucleotide Polymorphisms With Fluorescence Resonance Energy Transfer Detection, *Genetic Analysis: Biomolecular Engineering*, (1999) vol. 14, pp. 157–163.

Chen, Xiangning and Kwok, Pui–Yan; Template–directed Dye–terminator Incorporation (TDI) Assay: A Homogeneous DNA Diagnostic Method Based On Fluorescence Resonanace Energy Transer, *Nucleic Acids Research* (1997) vol. 25, No. 2, pp. 347–353.

Chen, Xiangning et al., A Homogenous, Ligase–Mediated DNA Diagnostic Test, *Genome Research* (1998) vol. 8, pp. 549–556.

Chen, Xiangning et al., Fluorescence Energy Transfer Detection As A Homogeneous DNA Diagnostic Method, *Proc. Natl. Acad. Sci. USA*, Sep. 1997, vol. 94, pp. 10756–10761.

Glazer, Alexander N. and Mathies, Richard A., Energy–Transfer Fluorescent Reagents For DNA Analyses, *Analytical Biotechnology*, (1997) vol. 8, No. 1, pp. 94–102.

Hung, Su–Chun et al., Cyanine Dyes With High Absorption Cross Section As Donor Chromophores In Energy Transfer Primers, *Analytical Biochemistry* (1996) vol. 243, pp. 15–27.

Hung, Su–Chun et al., Optimization Of Spectroscopic And Electrophoretic Properties Of Energy Transfer Primers, *Analytical Biochemistry*, (1997) vol. 252, pp. 78–88.

Hung, Su–Chun et al., Comparison Of Fluorescence Energy Transfer Primers, *Analytical Biochemistry* (1998) vol. 255, pp. 32–38.

Innis, Michael A. et al., DNA Sequencing With Thermus Aquaticus DNA Polymerase And Direct Sequencing Of Polymerase Chain Reaction–Amplified DNA, *Proc. Natl. Acad. Sci. USA*, Dec. 1988, vol. 85, pp. 9436–9440.

Ju, Jingyue et al., Energy Transfer Primers: A New Fluorescence Labeling Paradigm For DNA Sequencing And Analysis, *Nature Medicine* Feb. 1996, vol. 2, No. 2, pp. 246–249.

Ju, Jingyue, et al., Cassette Labeling For Facile Construction Of Energy Transfer Fluorescent Primers, *Nucleic Acids Research,* (1996) vol. 24, No. 6, pp. 1144–1148.

Ju, Jingyue et al., Design and Synthesis of Fluorescence Energy Transfer Dye–Labeled Primers and Their Application for DNA Sequencing and Analysis, *Analytical Biochemistry*, (1995) vol. 231, pp. 131–140.

Lee, Linda G.; Connell, Charles R. and Bloch, Will; Allelic Discrimination By Nick–translation PCR With Fluorogenic Probes, *Nucleic Acids Research*, (1993) vol. 21, No. 16, pp. 3761–3766.

Levedakou, Eleni, N.; Landegren, Ulf and Hood, Leroy E.; A Strategy To Study Gene Polymorphism By Direct Sequence Analysis Of Cosmid Clones And Amplified Genomic DNA, *Biotechniques*, (1989) vol. 7, No. 5, pp. 438–442.

Mead, D. A. et al., Bst DNA Polymerase Permits Rapid Sequence Analysis From Nanogram Amounts Of Template, *BioTechniques*, (1991) vol. 11, No. 1, pp. 76–87.

Prober, James M. et al., A System For Rapid DNA Sequencing With Fluorescent Chain–Terminating Dideoxynucleotides, *Science*, Oct. 16, 1987, vol. 238, pp. 336–341.

Risch, Neil and Merikangas, Kathleen; The Future Of Genetic Studies Of Complex Human Diseases, *Science*, Sep. 13, 1996, vol. 273, pp. 1516–1517.

Sanger, F., Nicklen, S. and Coulson, A. R.; DNA Sequencing With Chain–Terminating Inhibitors, *Proc. Natl. Acad. Sci. USA*, Dec. 1977, vol. 74, No. 12, pp. 5463–5467.

Wang, Yiwen et al., Microsatellite–based Cancer Detection Using Array Electrophoresis And Energy–transfer Fluorescent Primers, *Electrophoresis* (1997) vol. 18, pp. 1742–1749.

Wegmuller, B.; Luthy, J. and Candrian, U.; 3'–5' Proofreading–Induced Detection Of Point Mutations By PCR Using Tli DNA Polymerase, *Nucleic Acids Research*, (1995) vol. 23, No. 2, pp. 311–312.

Yu, Hongrun et al., Identification Of Human Plasma Kallikrein Gene Polymorphisms and Evaluation Of Their Role In End–Stage Renal Disease, *Hypertension* (1998) vol. 31, pp. 906–911.

\* cited by examiner

Exonuclease Digestion Products:

A Allele

```
           *
        5'-ACGTCGTTAGCATTACGAGCCAGTACACGATCCTACATCCTGCCGTCGTTAGCTACGAGCTAGATACG-3'
3'-AGGTCGATGCGAGTGAGTCGTTGCAGCAATCGTAATGCTCGGTCGTAGGATGTAGGACGGCAGCAATCGATGCTCGATCTATGC-5'
                                                                               \
                                                                                F
```

↓ Treat with: 5'-3' exonuclease

G Allele

```
           *
        5'-ACGTCGTTAGCATTACGAGCCAGTACACGATCCTACATCCTGCCGTCGTTAGCTACGAGCTAGATACG-3'
3'-AGGTCGATGCGAGTGAGTCGTTGCAGCAATCGTAATGCTCGGTCGTAGGATGTGCTAGGATGTAGGACGGCAGCAATCGATGCTCGATCTATGC-5'
                                                                                        \
                                                                                         F
```

↓ Treat with: Single stranded DNAse

Single Stranded Digestion Products:

A Allele

```
     *
  5'-ACGTCGTTAGCATTACGAGCCAGTACACGATCCTACATCCTGCCGTCGTTAGCTACGAGCTAGATACG-3'
  3'-TGCAGCAATCGTAATGCTCGGTCGTAGGATGTGCTAGGACGGCAGCAATCGATGCTCGATCTATGC-5'
                                                                        \
                                                                         F
```

G Allele

```
     *
  5'-ACGTCGTTAGCATTACGAGCCAGTACACGATCCTACATCCTGCCGTCGTTAGCTACGAGCTAGATACG-3'
  3'-TGCAGCAATCGTAATGCTCGGTCGTGATGTGCTAGGATGTAGGACGGCAGCAATCGATGCTCGATCTATGC-5'
                                                                           \
                                                                            F
```

↓ Denature and Separate by electrophoresis

Electrophoresis Results:

A allele    70 bp fragment
G allele    69 bp fragment

FIG. 1B.

Targets and Primers

Primer 1 ─── 5'-TCCAGCTACGCTCACTCAGC Variant Site
5'-...TACGTCCAGCTACGCTCACTCAGCAACGTCGTTAGCATTACGAGCAGCCAGTACACGATCCTACATCCTGCCGTCGTTAGCTACGAGCTAGATACGAT...-3'
3'-...ATGCAGGTCGATGCGAGTGAGTCGTTGCAGCAATCGTAATGCTCGGTCGTAGGATGTGCTAGGACGGCAGCAATCGATGCTCGATCTATGCTA...-5'

A Allele
Target [ 5'-...TACGTCCAGCTACGCTCACTCAGCAACGTCGTTAGCATTACGAGCAGCCAGTACACGATCCTACATCCTGCCGTCGTTAGCTACGAGCTAGATACGAT...-3'
        3'-...ATGCAGGTCGATGCGAGTGAGTCGTTGCAGCAATCGTAATGCTCGGTCGTAGGATGTGCTAGGACGGCAGCAATCGATGCTCGATCTATGCTA...-5'
                                                                                                            AATCGATGCTCGATCTATGC-5'——Primer 2
                                                                                                                              \\
                                                                                                                               F──Label G Allele
Target [ 5'-...TCCAGCTACGCTCACTCAGCGACGTCGTTAGCATTACGAGCAGCCAGTACACGATCCTACATCCTGCCGTCGTTAGCTACGAGCTAGATACGAT...-3'
        3'-...ATGCAGGTCGATGCGAGTGAGTCGCTGCAGCAATCGTAATGCTCGGTCGTAGGATGTGCTAGGACGGCAGCAATCGATGCTCGATCTATGCTA...-5'
                                                                                                            AATCGATGCTCGATCTATGC-5'
                                                                                                                              \\
                                                                                                                               F ↓ Amplification using dNTP mixes:
dATP, dTTP, dCTP, αSdGTP

90bp PCR Products:

A Allele
                    *
5'-TCCAGCTACGCTCACTCAGCAACGTCGTTAGCATTACGAGCAGCCAGTACACGATCCTACATCCTGCCGTCGTTAGCTACGAGCTAGATACG-3'
3'-AGGTCGATGCGAGTGAGTCGTTGCAGCAATCGTAATGCTCGGTCGTAGGATGTGCTAGGACGGCAGCAATCGATGCTCGATCTATGC-5'
                                                                                                     \\
                                                                                                      F G Allele
                    *
5'-TCCAGCTACGCTCACTCAGCGACGTCGTTAGCATTACGAGCAGCCAGTACACGATCCTACATCCTGCCGTCGTTAGCTACGAGCTAGATACG-3'
3'-AGGTCGATGCGAGTGAGTCGCTGCAGCAATCGTAATGCTCGGTCGTAGGATGTGCTAGGACGGCAGCAATCGATGCTCGATCTATGC-5'
                                                                                                     \\
                                                                                                      F

*FIG. 2A.*

METHODS FOR DETERMINING SINGLE NUCLEOTIDE VARIATIONS AND GENOTYPING

CROSS-REFERENCES TO RELATED APPLICATIONS

This application claims the benefit of U.S. Provisional Application No. 60/168,580, filed Dec. 12, 1999, which is incorporated herein in its entirety.

FIELD OF THE INVENTION

The present invention relates to the fields of molecular genetics and diagnostics.

BACKGROUND OF THE INVENTION

Many diseases linked to genome modifications, either of the host organism or of infectious organisms, are often the consequence of a change in a small number of nucleotides, frequently involving a change in a single nucleotide. Such single nucleotide changes are referred to as single nucleotide polymorphisms or simply SNPs, and the site at which the SNP occurs is typically referred to as a polymorphic site.

The ability to detect specific nucleotide alterations or mutations in DNA sequences is an important medical tool. The ability to identify such alterations provides a means for diagnosing many common diseases that are associated with SNPs, such as diabetes, thalassemia, sickle-cell anemia, cystic fibrosis, and certain oncogenic mutations. Methods capable of quickly identifying such changes or mutations are also valuable in taking prophylactic measures, assessing the propensity for disease and inpatient counseling and education.

Methods for determining which nucleotide is present at a polymorphic site are sometimes referred to as genotyping. Several methods are available for genotyping SNPs, including allele-specific oligonucleotide hybridization, mini-sequencing or primer extension, the TaqMan assay, and the oligo-ligation assay. However, frequently these methods include one or more shortcomings such as high cost, relatively long analysis times, use of radiolabeled reagents, complexity and/or being poorly suited for multiplex analysis wherein multiple analyses are conducted at the same time.

SUMMARY OF THE INVENTION

The present invention provides various methods and kits for determining the identity of a nucleotide at a variant site such as a polymorphism, for example. For instance, certain methods of the invention involve analyzing a variant site at which a first or second nucleotide in a target nucleic acid is located. Such methods include amplifying the target nucleic acid utilizing a first and second primer, wherein the first primer is complementary to a segment of a first strand of the target nucleic acid and the 3' end of the primer is adjacent to, but does not overlap, the variant site. The second primer is complementary to a segment of a second strand of the target nucleic acid and includes a nucleotide derivative resistant to digestion by a 5'-3' exonuclease. The first and second primers flank the variant site once they have hybridized to their respective strands.

Template-dependent extension of the first and second primers in the presence of four deoxynucleoside triphosphates (dATP, dTTP, dGTP and dCTP) is then conducted, wherein one of the deoxynucleoside triphosphates is an analog of a natural deoxynucleoside triphosphate that is resistant to digestion by 5'-3' exonucleases (e.g., a thiol base, a phosphorylated base or a boronated base). This deoxynucleotide analog is selected to be the complement of the first or second base at the variant site in the second strand and the target nucleic acid serves as a template such that an amplified double-stranded product is generated. The resulting double-stranded product is then digested with the 5'-3' exonuclease (e.g., phage T7 gene 6 exonuclease or lambda nuclease) to form a digested product having a single-stranded segment. The single-stranded segment in turn is removed with an enzyme that digests single-stranded DNA to produce a blunt end fragment. The size of the blunt-end fragment is then determined as an indicator of whether the variant site includes the first or second nucleotide.

The invention further provides related methods for conducting a multiplex analysis of multiple variant sites at the same time. For example, the invention provides certain methods for analyzing a first and second variant site in a first and second target nucleic acid, respectively. Each variant site can include a first or second base. Such methods generally begin by amplifying the first and second target nucleic acid by providing a first upstream and downstream primer pair. The first upstream primer is complementary to a segment of a first strand of the first target nucleic acid and its 3' end is adjacent to, but does not overlap the first variant site. The first downstream primer is complementary to a segment of a second strand of the first target nucleic acid and includes a nucleotide derivative resistant to digestion by a 5'-3' exonuclease. Upon hybridization to their respective strands, the first upstream and downstream primer flank the first variant site.

A second upstream and downstream primer pair are also provided. The second upstream primer is complementary to a segment of a first strand of the second target nucleic acid and the 3' end of the second upstream primer is adjacent to, but does not overlap, the second variant site. The second downstream primer is complementary to a segment of a second strand of the second target nucleic acid and includes a nucleotide derivative resistant to digestion by a 5'-3' exonucleases. The second upstream and downstream primer flank the second variant site once they hybridize to their respective strands.

Following hybridization of the primers, template dependent extension of the first and second primer pairs is conducted in the presence of four deoxynucleoside triphosphates (dATP, dTTP, dGTP and dCTP) wherein one of the deoxynucleoside triphosphates is an analog of a natural deoxynucleoside triphosphate that is resistant to digestion by 5'-3' exonucleases. This deoxynucleotide analog is selected to be the complement of the first or second base at the first and second variant site in the second strand of the first and second target nucleic acids. The first and second target nucleic acid each serve as a template, such that an amplified double-stranded product is generated from each of the first and second primer pairs, thereby generating a plurality of double-stranded products.

Thee plurality of double-stranded products is digested with the 5'-3' exonuclease to form a plurality of digested products, each having a single-stranded segment which is removed with an enzyme that digests single-stranded DNA. This digestion reaction produces a plurality of blunt end fragments. The size of these fragment is determined to identify whether the first and second variant sites include the first or second base.

In another aspect, the invention provides kits for analyzing a variant site in a target nucleic acid. Certain kits of the invention include a deoxynucleotide analog for use in primer extension reactions which when incorporated into an extension product is resistant to digestion by 5'-3' exonucleases, a 5'-3' exonuclease and an enzyme that digests single-stranded DNA. In some kits, the deoxynucleotide analog is a thiol base, a phosphorylated base or a boronated analog. Still other kits further include an enzyme that digests single-stranded DNA (e.g., mung bean nuclease and S1 nuclease). The kits may also contain two primers. If included in the kit, one primer is complementary to a segment of a first strand in the target nucleic acid such that the 3' end of the primer is adjacent to, but does not overlap, the variant site of the target. The second primer is complementary to a downstream segment of a second strand of the target nucleic acid and includes a nucleotide analog derivative that is resistant to digestion by an exonuclease.

BRIEF DESCRIPTION OF THE DRAWINGS

FIGS. 1A–1B illustrate the different steps of a method according to the present invention for an A/G polymorphism wherein the extension reaction is conducted using the nucleotide derivative α-SdATP and the standard nucleotides dTTP, dCTP and dGTP. The nucleotide derivative incorporated into the amplification product is shown with an asterisk (*). FIG. 1A: Primers=SEQ ID NOS:1 and 3; Targets=SEQ ID NOS:2, 4 and 5; 90 bp PCR Products=SEQ ID NOS:6 and 7. FIG. 1B: Exonuclease Digestion Products=SEQ ID NOS:8–11; Single Stranded Digestion Products=SEQ ID NOS:8 and 10.

FIGS. 2A–2B illustrate the different steps of a method according to the present invention for an A/G polymorphism wherein the extension reaction is conducted using the nucleotide derivative α-SdGTP and the standard nucleotides dTTP, dCTP and DATP. The nucleotide derivative incorporated into the amplification product is shown with an asterisk (*). FIG. 2A: Primers=SEQ ID NOS:1 and 3; Targets=SEQ ID NOS:4 and 5; 90 bp PCR Products=SEQ ID NOS:6 and 7. FIG. 2B: Exonuclease Digestion Products=SEQ ID NOS:12, 9, 13 and 11; Single Stranded Digestion Products=SEQ ID NOS:12 and 13.

DETAILED DESCRIPTION

I. Definitions

Figure 1A:
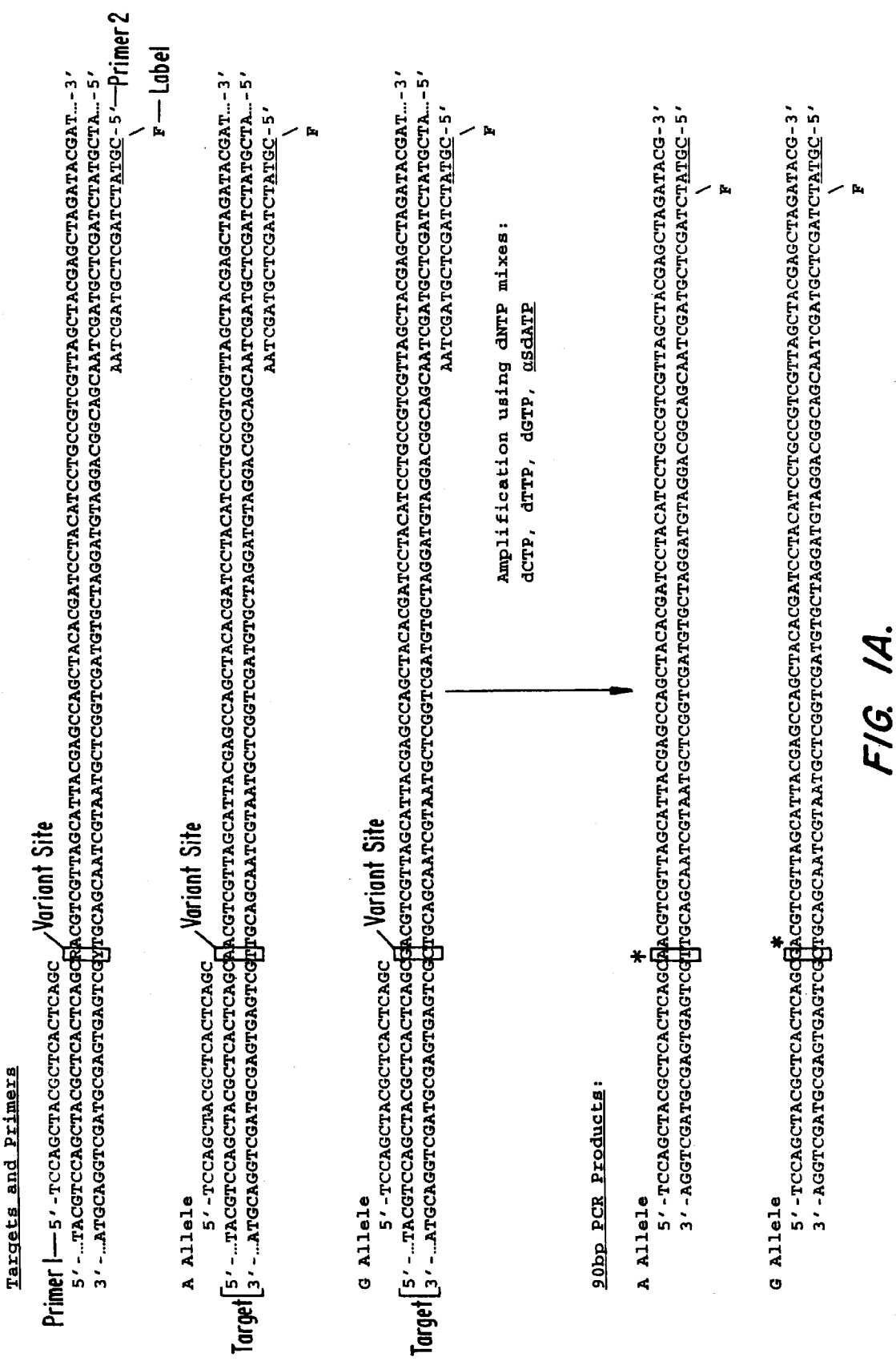

A "nucleic acid" is a deoxyribonucleotide or ribonucleotide polymer in either single or double-stranded form, including known analogs of natural nucleotides unless otherwise indicated.

A "polynucleotide" refers to a single- or double-stranded polymer of deoxyribonucleotide or ribonucleotide bases.

An "oligonucleotide" is a single-stranded nucleic acid ranging in length from 2 to about 500 bases. Oligonucleotides are often synthetic but can also be produced from naturally occurring polynucleotides. Oligonucleotides can be prepared by any suitable method, including, for example, cloning and restriction of appropriate sequences and direct chemical synthesis by a method such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetrahedron Lett.* 22:1859–1862 (1981); and the solid support method of U.S. Pat. No. 4,458,066.

A "primer" is a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer site" refers to the segment of the target DNA to which a primer hybridizes. The term "primer pair" means a set of primers including a 5' "upstream primer" that hybridizes with the 5' end of the DNA sequence to be amplified and a 3' "downstream primer" that hybridizes with the complement of the 3' end of the sequence to be amplified. When reference is made to a primer hybridizing "adjacent to" a nucleotide site, it is meant that the primer preferably hybridizes immediately 5' to the site, or optionally, that the primer hybridizes 5' to the site, so long as the nucleotide base that appears at the variant site of the template strand does not appear in the region between the 3' end of the primer and the variant site of the template strand.

A "variant site" broadly refers to a site wherein the identity of nucleotide at the site varies between nucleic acids that otherwise have similar sequences. For double-stranded nucleic acids, the variant site includes the variable nucleotide on one strand and the complementary nucleotide on the other strand. A variant site can be the site of a single nucleotide polymorphism or the site of a somatic mutation, for example.

A "polymorphic marker" or "polymorphic site" is the locus at which divergence occurs. Preferred markers have at least two alleles, each occurring at frequency of greater than 1%, and more preferably greater than 10% or 20% of a selected population. The first identified allelic form is arbitrarily designated as the reference form and other allelic forms are designated as alternative or variant alleles. The allelic form occurring most frequently in a selected population is sometimes referred to as the wildtype form, whereas allelic forms occurring less frequently are referred to as mutant alleles. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

II. General

The invention provides methods and kits for identifying the nucleotide present at a variant site. Thus, for example, the methods can be used to identify which allele is present at a single nucleotide polymorphic (SNP) site. Because many diseases are associated with SNPs, the methods can be used in a variety of diagnostic, research and prognostic applications. In addition, for diploid subjects, the methods can be used to determine if the subject is homozygous or heterozygous for a particular allele at the variant site. This is an important capability because individuals that are homozygous for a mutant allele associated with a disease are at greater risk than individuals that are heterozygous or homozygous for the wildtype allele. Furthermore, individuals that are homozygous mutants for an allele associated with a particular disease sometimes suffer the symptoms of the disease to a greater extent than heterozygotes.

In general, the methods of the invention begin with template-dependent amplification of a target sequence under defined conditions to achieve selective incorporation of a nucleotide analog at a variant site. The amplification product is then subjected to limited degradation to create products having allele-specific sizes. Finally, the number of products and their sizes is assessed to determine the identity of the nucleotide(s) at the variant site and, when a sample is taken from a diploid organism, whether the organism is a heterozygote or homozygote (either mutant or wild type).

Through the use of multiple primer pairs to amplify different segments of a nucleic acid or nucleic acids, multiple analyses can be conducted at the same time in certain methods. For example, the methods of the invention can be used to determine the identity of the nucleotide at multiple variant sites on a single nucleic acid or at multiple variant sites on different nucleic acids. This multiplexing feature enables certain methods to achieve very high throughput.

III. Determination of a Nucleotide at a Single Variant Site

A. General Description

In the methods described herein, when a specific type of polymorphism or variant site is referred to, the nucleotides indicated as being in the polymorphic or variant site are those present in the amplified strand that includes the variant site primer (see below). Similarly, when a specific base or nucleotide is referred to as being at a variant site, the referenced nucleotide is the one in the strand that includes the variant site primer.

Certain methods of the invention include determining which allele or nucleotide is present at a single variant site, such as an SNP (including somatic and germline mutations) or a somatic mutation for example. A specific example of such methods are illustrated in FIGS. 1A and 1B wherein the variant site is an A/G polymorphic site (i.e., the variant site includes an A or G). Although the method is described with reference to a particular polymorphism, it should be appreciated that the methods are generally applicable to determining the identity of a nucleotide at any variant site.

As shown in FIGS. 1A and 1B, the method begins with the amplification of a target nucleic acid using two primers that flank the variant site. One of the primers is complementary to a segment of a first strand of the target nucleic acid and its 3' end extends adjacent to, but does not overlap, the variant site being analyzed (the "variant site primer;" e.g., primer 1 in FIGS. 1A and 1B). In the particular example shown in FIG. 1A, the variant site primer extends to the nucleotide that is immediately 5' to the variant site. However, as described in greater detail below, this is not always necessary. The second primer (also called the "modified primer") is modified so it is resistant to digestion by a 5'-3' exonuclease. Typically, this modification involves incorporating a nucleotide derivative that is resistant to 5'-3' exonuclease activity into the modified primer. The second primer also generally includes a label to facilitate detection of the ultimate products (see below), but a label is not required.

Template-dependent extension of the primers is conducted in the presence of the standard four deoxynucleoside triphosphates (i.e., dATP, dTTP, dCTP, dGTP), with the exception that one deoxynucleoside triphosphate (dNTP) is a dNTP analog that is resistant to degradation by a 5'-3' exonuclease. The dNTP supplied in analog form is selected to be complementary to the nucleotide at the variant site in the strand that serves as the template for extension of the variant site primer. Thus, for the example depicted in FIGS. 1A and 1B which is for an A/G polymorphism (i.e., the variant site includes A or G), the dNTP analog used during the extension reaction is chosen to be either a dATP or dGTP analog (these analogs are complementary to the T or C nucleotides, respectively, in the strand that serves as a template for the variant site primer). Similarly, for a T/C polymorphism (i.e., the variant site includes either a T or C allele), then the dNTP analog can be either a dTTP or dCTP analog (these analogs are complementary to the A or G nucleotide, respectively, in the strand that serves as a template for the variant site primer).

Various dNTP analogs can be used in the extension reaction so long as they are resistant to degradation by a 5'-3' exonuclease and do not interfere with the template-dependent extension reaction. Examples of such analogs include nucleotides wherein the base, sugar or phosphate group that becomes part of the phosphodiester bond are modified. One specific example of a suitable analog is one in which an oxygen atom attached to the alpha phosphorous is replaced with a sulfur atom, represented as a-SdNTP and sometimes simply referred to as a "thiol base." Thus, as shown in FIGS. 1A and 2A, the analog is $\alpha$-SdATP or $\alpha$-SdGTP, respectively. Another option includes boronated nucleotides wherein the sugar or base is attached via a linker to a boron moiety, for example.

FIGS. 1A and 1B show the situation in which amplification is performed in the presence of ($\alpha$-SdATP). Assuming both variant forms of the nucleic acid are present (e.g., the sample is taken from a diploid organism and the A and G allelic forms are both present because the organism is a heterozygote), amplification yields two amplification products. If only one allelic form is present in a sample (e.g., the organism is diploid but a homozygote), then only a single amplification product is obtained. As shown in FIG. 1A, when the nucleotide A is present at the variant or polymorphic site, a thiol A nucleotide from $\alpha$-SdATP is incorporated at the variant site. However, when the variant site includes the nucleotide G, the thiol A nucleotide from $\alpha$-SdATP is not incorporated at the variant site, but instead is incorporated at the next occurrence of the nucleotide A. For the target shown in FIG. 1A, the next A nucleotide is immediately 3' of the variant site. The nucleotide analog is represented with an asterisk (*).

The resulting double-stranded amplified products are then digested with a 5'-3' exonuclease. The strand into which the dNTP analog is incorporated during the extension reaction is digested up to, but not including, the nucleotide analog that is resistant to 5'-3' exonuclease activity. In the instance in which an $\alpha$-SdNTP nucleotide is used, the 5'-3' exonuclease is unable to cleave the thiol linkage. Similarly, the nucleotide derivative at the 5' end of the modified primer prevents the 5'-3' exonuclease from degrading the strand into which the modified primer is incorporated.

With reference now to FIG. 1B, for the A allelic form the 5'-3' exonuclease stops cleaving once the nucleotide immediately 5' to the variant site is removed. For the G allelic form, the exonuclease stops cleaving once the nucleotide at the variant site is removed. Hence, for the G allelic form, one additional base is removed relative to the A allelic form. As described above, the 5' end of the other strand of the amplified product is not digested because the 5' end of the modified primer is modified to prevent such digestion.

Digestion by the 5'-3' exonuclease generates digested amplification products that have a single-stranded segment (see FIG. 1B). These single-stranded segments are removed through the activity of a single-stranded nuclease that digests the single-stranded DNA to produce double-stranded blunt end fragments. Because the dNTP analog is incorporated into the amplification product in an allele-specific manner, it is possible to determine which nucleotide is present at the variant site by determining the size of the resulting fragments. Typically, the size of the fragments is determined by denaturing the double-stranded fragments and then separating the different sized fragments by electrophoresis, although various other options are available (see below).

For the A/G polymorphic site in the target nucleic acid shown in FIGS. 1A and 1B, a 70 bp fragment is formed when the nucleotide A is at the variant site, and a 69 bp fragment is formed when the nucleotide G is present at the variant site. If the sample is acquired from a diploid organism, then fragments of both size are formed. If, however, the organism is a homozygote, then only fragments of a single size are formed (a 70 bp fragment for a homozygote bearing the A allele and a 69 bp fragment for a homozygote bearing the G allele).

Figure 2B:
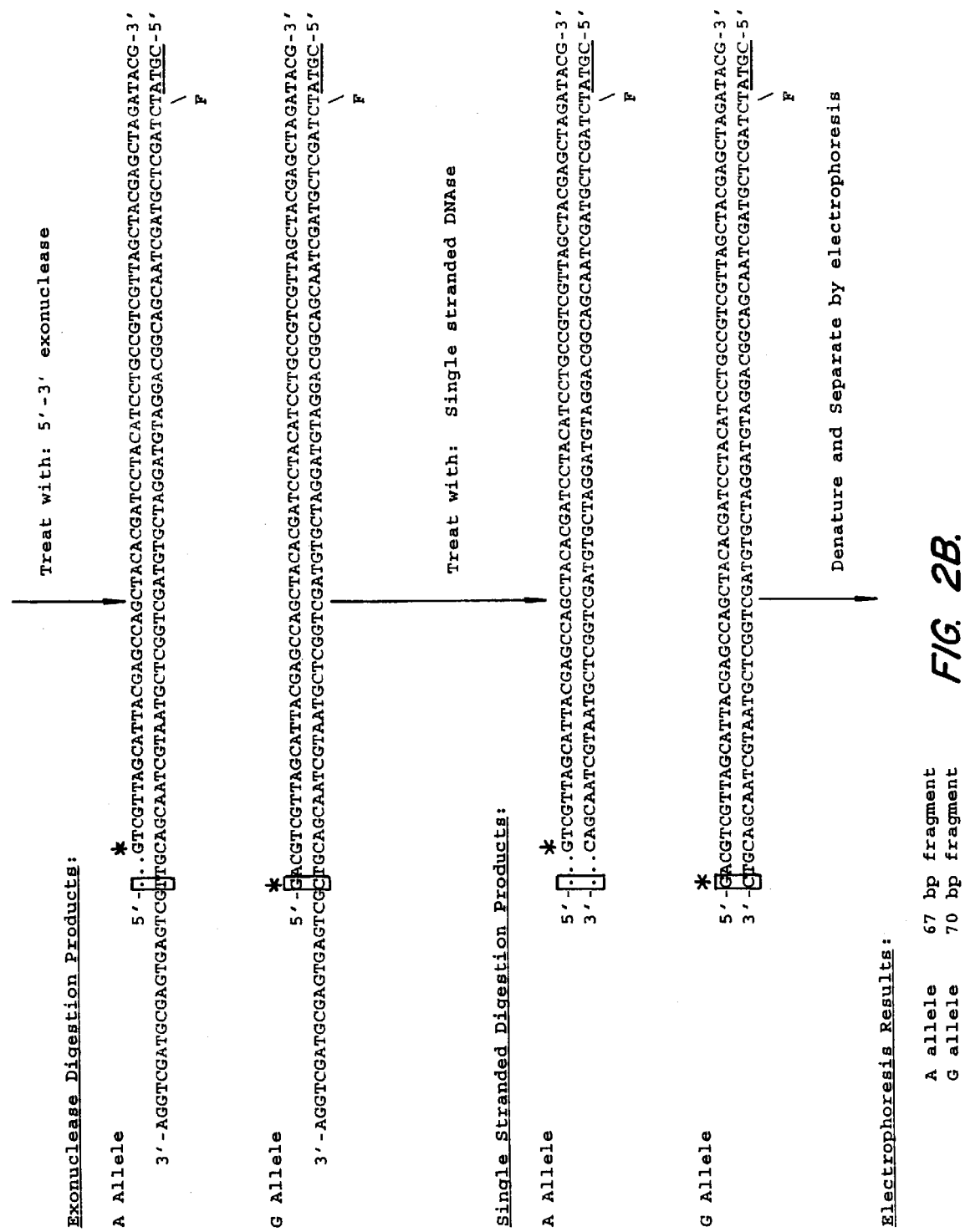

FIGS. 2A and 2B show the same process with the same target nucleic acids wherein the variant site still includes A or G as shown in FIGS. 1A and 1B; however, in this instance, amplification is conducted using an analog of G ($\alpha$-SdGTP) instead of $\alpha$-SdATP. In this instance, the thiol base is not incorporated at the variant site during amplification of the A allelic form, but instead at the next occurrence of the nucleotide G. For the target nucleic acid shown in FIG. 2A, this means that a thiol base is not incorporated until 3 nucleotides downstream of the variant site. Of course, for G allelic forms wherein the variant site includes G, $\alpha$-SdGTP is incorporated at the variant site (see FIG. 2A). Hence, as shown in FIG. 2B, after treatment with the 5'-3' exonuclease and the single-stranded nuclease, a 67 bp fragment is generated for the A allelic form under these conditions; whereas, a 70 bp fragment is generated for the G allelic form. Assuming the organism from which the target nucleic acids is obtained is diploid, both fragments are only formed if the organism is a heterozygote. If the organism is a homozygote at this particular allele, only a single-sized fragment is formed (a 67 bp fragment for a homozygote bearing the A allele and a 70 bp fragment for a homozygote bearing the G allele).

As explained above, the methods can be performed using nucleotide analogs that are complementary to any of the nucleotides that appear at the variant site in the strand that serves as a template for the variant site primer. However, as the examples just described illustrate, differing sized fragments are generated depending upon which nucleotide analog is utilized during the amplification process. In the foregoing examples, a 70 bp and 69 bp fragment are generated when $\alpha$-SdATP is used (assuming the sample is from a heterozygote); whereas, a 70 bp and 67 bp fragment are generated when $\alpha$-SdGTP is utilized (again, assuming the sample is from a heterozygote). Although the methods are capable of distinguishing both fragments in either set of fragments, the larger difference in sizes between fragments in the latter case makes it the preferable approach in this particular instance. Hence, the choice of which nucleotide analog to use in a particular experiment is informed by the identity of the nucleotide at the variant site in the template strand, as well as which analog results in the formation of fragments having the largest difference in size.

B. Methods with More than Two Allelic Forms

The foregoing examples have been described for a biallelic situation in which the variant site includes one of two different nucleotides. However, the same general approach can be used in those instances in which the variant site consists of more than two allelic forms. For example, in a triallelic case, the nucleotide analog can correspond to any one of three alleles. Thus, for example, if the variant site includes A, G, and T allelic forms, then the analog used in the amplification reaction can be $\alpha$-SdATP, $\alpha$-SdGTP or $\alpha$-SdTTP. However, whereas the presence of diallelic forms can be determined with a single analysis, distinguishing between triallelic forms requires two analyses (i.e., two amplification reactions with different nucleotide analogs). Thus, in the foregoing example for a triallelic form wherein the variant site includes A, G or T, amplifications are run with analogs of the following pairs of nucleotides: A and G, A and T, or G and T, a separate amplification being run with each nucleotide analog of the pair. As just described above, the pair of analogs that gives the best results (i.e., the largest variation in amplified product size) depends upon the sequence adjacent the variant site.

C. Genotyping

A diploid organism contains two copies of each gene, and thus has two copies of the target DNA that is amplified according to the methods described herein. Genotyping involves the determination of whether a diploid organism contains two copies of the wild type allele (a wild type homozygote), one copy each of the wild type and mutant allele (i.e., a heterozygote), or contains two copies of the mutant allele (i.e., a mutant homozygote). As demonstrated in FIGS. 1A to 2B, the methods of the present invention can establish the genotype of an organism from the number and size of amplification products formed. For a diallelic situation, the genotype can be determined in a single reaction; a triallelic form requires only two reactions. This feature of certain methods of the invention means that only relatively small amounts of sample are required to conduct an analysis and enables samples to be analyzed on a high throughput basis.

For instance, in the example shown in FIGS. 1A and 1B, a 70 bp fragment is formed if amplifications are conducted with $\alpha$-SdATP and the variant site includes the A allele; whereas, a 69 bp fragment is generated if the variant site is of the G allelic form. Assuming that the A allele is the wildtype form, if only a 70 bp fragment is obtained, then the organism is a wildtype homozygote. If only a 69 bp fragment is formed, then the organism is a mutant homozygote. The formation of a 70 bp and 69 bp fragment means that the organism is a heterozygote. Similarly, a 67 bp fragment is formed if amplifications are conducted with $\alpha$-SdGTP and the variant site includes an A allele, while a 70 bp fragment is formed if the variant site includes a G allele. Thus, under these conditions, the formation of only a 67 bp fragment or only a 70 bp fragment means that the organism is a wildtype homozygote or a mutant homozygote for the allele tested, respectively. The formation of both a 67 and 70 bp fragment means that the organism is a heterozygote and a carrier of the mutant allele.

The ability to make such facile determinations provides a powerful tool in genetic analysis and ascertaining the susceptibility of an individual to a disease. Individuals that are mutant homozygotes for an allele associated with a particular disease are at higher risk of obtaining the disease than a heterozygote or a wild type homozygote. The heterozygote, however, is a carrier of the allele associated with the disease. Such knowledge can be useful in prenatal and other types of medical and genetic counseling, for example.

IV. Multiplexing

The invention also provides methods for conducting genotyping analyses in a multiplex format in which the identity of an allele at multiple variant sites can be determined simultaneously. The multiple sites can be multiple different sites on the same target nucleic, the same site on the same target nucleic acid from different test individuals, or multiple different sites on different target nucleic acids from multiple test individuals, so long as the potential nucleotides at the different variant sites are the same at each site (e.g., all the mutant sites are A/G polymorphisms). Typically, the sites being analyzed are sufficiently distant from one another that the binding sequences for the primers do not overlap, although this is not a requirement.

The methods closely parallel those for determining which nucleotide is present at a single variant site, except that one or more additional primer pairs are also provided so that amplification of various segments of DNA containing different variant sites occur at the same time. For example, in addition to the first and second primers described above (i.e., the first upstream and downstream primer pair), at least one additional primer pair (a second upstream and downstream primer pair) is also provided. The upstream and downstream primers of the first primer pair hybridize with the first and second strand of the first target nucleic acid as set forth above. Similarly, the upstream primer of the second primer pair is complementary to and hybridizes with a segment of a first strand of a second target nucleic acid; the downstream primer of the second primer pair is complementary to and hybridizes with the second strand of the second target nucleic acid. The primers that anneal to the second strands of the target nucleic acids are modified to be resistant to 5'-3' exonuclease activity and typically include a label. The two members of the second primer pair once hybridized to the second target nucleic acid flank a second variant site.

Template-dependent extension is performed as described above. Thus, the nucleotide provided in analog form is the complement of one of the nucleotides that occurs at the variant site of the strand that serves as a template for the extension of the variant site primer (i.e., upstream primer). Amplification in this instance yields a plurality of different double-stranded amplification products that are then digested with the 5'-3' exonuclease and a single-stranded nuclease as described above to produce a plurality of different blunt end fragments that are of allele-specific sizes. Thus, by determining the size of the fragments it is possible to identify which nucleotide is present at the various variant sites.

If the different fragments are separated by gel electrophoresis, the modified primers (i.e., the downstream primers of the primer pairs) generally include labels to facilitate detection. Although the labels can be the same, more typically the labels are of different types (e.g., different fluorophores that emit at different wavelengths) to aid in distinguishing which electrophoretic band is associated with each of the various variant sites. Thus, for example, if several different polymorphic sites are to be examined on either a single nucleic acid or multiple target nucleic acids, the downstream primer for each variant site can be labeled with a different fluorophore that produces a unique color. Once final fragments are separated on a gel for example, it is possible to correlate rapidly the different fragments with the different variant sites based upon the color of the different electrophoretic bands.

V. Amplification

A. General

Amplification procedures begin with the acquisition of nucleic acid sample. If double stranded, the nucleic acid is first denatured to form single-stranded nucleic acid using any of a variety of denaturation techniques which are known in the art, including, for example, physical, chemical, enzymatic or thermal means. Typically, strand separation is achieved using heat denaturation at temperatures ranging from 80° C. to about 105° C. for time periods ranging from about 1 to 10 minutes. For cases in which the nucleic acid is RNA, the sample may first be reverse transcribed to form cDNA which is then denatured.

The resulting denatured nucleic acid strands are incubated with the primers under hybridization conditions, i.e., conditions in which the primers anneal to their respective complementary portions of the single-stranded nucleic acid. Because the denatured nucleic acid strands are typically considerably longer than the primers, there is an increased probability that a denatured strand makes contact and reanneals with its complementary strand before the primer or probe has a chance to hybridize to their complementary sequences. To avoid this problem, a high molar excess of primer and probe (if utilized) are used to increase the likelihood that they anneal to their respective template strand before the denatured strands reanneal.

Amplification is typically conducted the using polymerase chain reaction (PCR) according to known procedures. See generally PCR Technology: Principles and Applications for DNA Amplification (ed. H. A. Erlich, Freeman Press, NY, N.Y., 1992); PCR Protocols: *A Guide to Methods and Applications* (eds. Innis, et al., Academic Press, San Diego, Calif., 1990); Mattila et al., *Nucleic Acids Res.* 19: 4967 (1991); Eckert et al., PCR *Methods and Applications* 1: 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4:560 (1989), Landegren et al., *Science* 241:1077 (1988), transcription amplification Kwoh et al., *Proc. Natl. Acad. Sci. USA* 86:1173 (1989)), and self-sustained sequence replication (Guatelli et al., *Proc. Nat. Acad. Sci. USA* 87:1874 (1990)) and nucleic acid based sequence amplification (NASBA).

B. Primers

1. General

One primer is selected to have a sequence that is complementary to the sequence upstream of the variant site. The other primer is chosen to have a sequence that is complementary to a sequence in the other strand of the duplex DNA being amplified. As indicated above, the two primers flank the variant site once they have hybridized to their respective strands. The primers are generally 15 to 30 nucleotides long, and more typically are about 20 to 24 nucleotides long. However, the length of the primers can be larger or smaller depending upon the particular sequence to which they hybridize. The distance between the 3' end of the first primer and the 3' end of the second primer when the primers are hybridized to their respective strands can vary widely. In general, the distance is from 5 to about 1000 base pairs or more; in other instances, the separation distance is from about 5 to 700 base pairs. In still other instances in which the size of the allelic products only differs by a limited number of bases, it is advantageous to have the distance between the primers towards the lower end of the range so that the size difference is a larger proportion of the overall size of the fragments. This makes distinguishing between the different products somewhat easier.

2. Variant Site Primer

The sequence of the first primer is often selected so that its 3' end hybridizes to the nucleotide that is just 5' to the variant site. However, as noted above, this is not required. The 3' end of the first primer can be positioned several nucleotides 5' of the variant site, so long as the nucleotide at the variant site in the template strand for the variant site primer does not occur in the segment of nucleotides extending from the 3' end of the first primer to the variant site on the template strand for the variant primer. For example, referring again to FIG. 1A, the sequence on either side of the variant site in the template strand for primer 1 is as shown below for the situation in which the nucleotide T is located at the variant site (variant site is underlined and is the sequence for the A allelic form of the polymorphism):

. . . TCGATGCGAGTGAGTCG<u>T</u>TGC . . . (second/ template strand) (SEQ ID NO:14)

The primer . . . AGCTACGCTCACTCA (SEQ ID NO:15) is a suitable primer because, as shown below, it hybridizes to the template strand to give a structure in which there are no T nucleotides in the segment of the template strand for the variant primer that extends from the 3' end of the primer to the variant site. Consequently, no α-SdATP is incorporated into the amplified product upstream from the variant site and the proper allele-specific sized fragment is generated.

5' . . . AGCTACGCTCACTCA (SEQ ID NO:15)

3' . . . TCGATGCGAGTGAGTCG<u>T</u>TGC . . . 5' (second/ template strand) (SEQ ID NO:14)

However, the first primer could not have the sequence . . . AGCTACGCTCACTC (SEQ ID NO:16), because hybridization of this primer yields structure in which there is a T nucleotide (shown in bold type) in the segment of the template strand that extends opposite from the 3' end of the primer to the variant site.

5' . . . AGCTACGCTCACTC (SEQ ID NO:16)

3' . . . TCGATGCGAGTGAGTCG<u>T</u>TGC . . . 5' (second/ template strand) (SEQ ID NO:14)

If α-SdATP where utilized in the extension reaction, the thiol nucleotide would be incorporated into the amplified product upstream from the variant site (opposite the nucleotide in bold type) and the proper allele-specific sized fragment would not be generated, since the exonuclease would stop prior to the variant site.

The same analysis applies in the instance in which G is the nucleotide located at the variant site of the first strand. Generally, primers not extending to the nucleotide immediately 5' to the variant site can be used, so long as no G nucleotides occur in the segment of nucleotides extending from the 3' end of the first primer to the variant site on the template strand for the variant site primer. For the sequence shown in FIG. 1A, however, a G nucleotide (bold type) immediately precedes the one located at the variant site (underlined). Thus, in this particular instance, the primer should extend to the nucleotide immediately 5' to the variant site.

. . . TCGATGCGAGTGAGTCG<u>G</u>TGC . . . (second/ template strand) (SEQ ID NO:17)

3. Second Primer

The other primer used in amplification of the target sequence is modified so as to make it resistant to cleavage by a 5'-3' exonuclease. As described above for the nucleotide analog, this can be accomplished in a number of ways, such as by modifying the sugar, base or phosphodiester linkage. For example, a nucleotide analog can be used in the primer that forms a cleavage-resistant bond to an adjacent nucleotide (e.g., a phosphorothioate linkage). Although many 5'-3' exonucleases can remove a base that is either phosphorylated or not phosphorylated, λ 5'-3' exonuclease can cleave only phosphorylated strands. Thus, another option for blocking 5'-3' exonuclease activity is to utilize a primer that is not phosphorylated in combination with λ 5'-3' exonuclease. Other options involve utilizing primers that include a boronated analog (i.e., a primer in which a boron compound is linked to a nucleotide sugar or base, for example) or 3'-O,4'-C-methyleneribonucleosides.

The second primer is optionally labeled. The label can occur at any nucleotide in the primer so long as it does not interfere with the primer extension reaction. In some instances, the label is attached to a nucleotide via a linker. A variety of suitable linkers are commercially available from Pierce Chemical Company in Rockford, Ill. and are described in EP 188,256; U.S. Pat. Nos. 4,671,958; 4,659, 839; 4,414,148; 4,669,784; 4,680,338; 4,569,789; and 4,589,071. The type of label can vary so long as it generates a signal that is detectable during the size determination step. Examples of suitable labels include, fluorophores, chromophores, magnetic particles, radioisotopes, and a mass marker.

A variety of fluorescent molecules are well-suited for use as labels including, for example, fluorescein and fluorescein derivatives, rhodamine and rhodamine derivatives, naphythylamine and naphthylamine derivatives, cyanine and cyanine derivatives and bodipy dyes. Specific examples of fluorescent dyes include 3-(ε-carboxypentyl)-3'-ethyl-5, 5'-dimethyloxa-carbocyanine (CYA), 6-carboxy fluorescein (FAM), 5&6-carboxyrhodamine-110 (R110), 6-carboxyrhodamine-6G (R6G), N',N',N',N'-tetramethyl-6-carboxyrhodamine (TAMRA), 6-carboxy-X-rhodamine (ROX), 2',4',5',7',-tetrachloro-4-7-dichlorofluorescein (TET) and 2',7'-dimethoxy-4',5'-6 carboxyrhodamine (JOE).

VI. Digestion Reactions

Digestion of the amplification products with the 5'-3' exonuclease and the single-stranded nuclease can be performed as two discrete steps. More typically, however, the two enzymes are allowed to digest the amplified products at the same time. Thus, the methods can be performed with a single post amplification step in a single reaction container that enhances the high throughput capabilities of the invention.

A variety of 5'-3' exonucleases can be utilized. Two which are commercially available include λ 5'-3' exonuclease (available from, for example, Amersham or Boehringer Mannheim) and phage T7 gene 6 5'-3' exonuclease (available from, for example, Amersham). A T5 5'-3' exonuclease can also be utilized and can be obtained as described by Kaliman A. V., et al., FEBS Lett. 195:61–64 (1986), and Ceska T. A., et al., J. Mol. Biol. 233:179–82 (1993). Many DNA polymerases also have a 5'-3' exonuclease activity and can be used.

The single-stranded nuclease can be any nuclease capable of removing single-stranded overhangs. Examples include mung bean nuclease and S1 nuclease, both of which are commercially available from Amersham and Boehringer Mannheim, for example.

VII. Size Determination

Various approaches can be taken to determine the size of the final fragments obtained following the digestion reactions. In general, any method capable of distinguishing between nucleic acids that vary in size can be utilized, especially those capable of distinguishing between small differences in size. Separation by electrophoresis is one useful approach. In some methods, the double-stranded fragments formed from the digested reactions are first denatured to form single strands. This can be accomplished by a variety of standard methods, including, for example, heating the mixture containing the fragments at approximately 95° C. for about 5 minutes, or by subjecting the mixture to basic conditions. Separation of the fragments into single strands is not required, however. In other methods, the double stranded fragments are electrophoresed directly.

Various types of electrophoresis can be utilized to effect the separation. For example, various matrixes can be utilized in the separation, such as agarose and acrylamide gels. The electrophoretic separation can be achieved using capillary electrophoresis or microchannel formats, for example. In certain methods, all of the various steps of the method are integrated into a single device. Hence, the amplification, digestion and separation steps are all accomplished using a microchannel device that allows the analyses to be conducted rapidly with only minute amounts of sample.

If the second primer contains a label, electrophoretic bands can be detected directly. If a method is performed with a primer lacking a label, then the band(s) can be visualized using known dye staining techniques. As indicated above, in multiplex assays conducted using labels of different colors, bands of a particular color can be correlated with particular variant sites.

Instead of using electrophoresis, the size of the bands can also be determined by mass spectroscopy. In such instances, the digested fragments are taken up into an appropriate buffer and injected into the mass spectrometer for analysis.

VIII. Sample Types

Polymorphisms are detected in a target nucleic acid from an individual being analyzed. For assay of genomic DNA, virtually any biological sample (other than pure red blood cells) is suitable. For example, convenient tissue samples include whole blood, serum, semen, saliva, tears, urine, fecal material, sweat, buccal, skin, spinal fluid and hair; samples can also be derived from in vitro cell cultures, including the growth medium, recombinant cells and cell components. For assay of cDNA or mRNA, the tissue sample must be obtained from an organ in which the target nucleic acid is expressed. For example, if the target nucleic acid is a cytochrome P450, the liver is a suitable source.

Preparation of the sample prior to amplification is according to known methods such as those described in Sambrook, et al., *Molecular Cloning: A Laboratory Manual*, $2^{nd}$ Ed., Cold Spring Harbor Laboratory Press, (1989).

IX. Applicability

The methods described herein are useful for identifying whether a nucleic acid from a particular subject includes a wild type allele or a mutant allele at a particular SNP site. Furthermore, in a single analysis, the methods can be utilized to establish the genotype of the individual being tested (i.e., distinguish whether the individual is a wild type homozygote, a heterozygote or a mutant homozygote). The methods are also useful for identifying somatic point mutations, and can be used to identify mutations associated with various diseases.

The genotyping utility of the present methods makes them useful within the context of medical diagnosis and prognosis. Since many SNPs are associated with various diseases, clinicians can utilize the results of the genotype study to assess the presence of disease, whether an individual is a carrier of disease, the likelihood that an individual will get a particular disease and the efficacy of various treatment alternatives. As indicated above, individuals that are mutant homozygotes for a particular allele are the most susceptible of acquiring a disease associated with the mutant allele. A heterozygote is at risk, but at less risk than a mutant homozygote.

A. Correlation Studies

Use of the methods of the present invention to acquire diagnostic information involves obtaining a sample from a number of different individuals known to have a common disease and conducting screening tests to determine whether they consistently share a common genotype at one or more SNP sites. The results of such screening can be used to establish correlations between certain genotypes and certain diseases.

In a related fashion, the methods of the invention can be used to develop correlations between certain genotypes and patient prognosis. For example, the genotype of a population of individuals suffering from a common disease can be determined at one or more SNP sites. The health history of the individuals can be monitored with time to establish correlations between certain genotypes and disease outcomes.

The methods of the invention can also be used to formulate optimal treatment protocols for a particular disease. The methods described herein can be used to place individuals into groups that share a common phenotype and genotype. The group can then be subdivided into various groups that each receive various forms of treatment. By monitoring the health status of the different treatment groups over time, the most effective treatment program for a particular genotype can be established.

B. Use of Current Methods as Screening and Therapeutic Tool

In instances in which a correlation between a particular genotype and disease state have already been established, the methods of the invention can be utilized as a diagnostic tool, a prognostic tool and as a means for assessing the success of various treatment options.

For patients having symptoms of a disease, the methods of the present invention can be used to determine if the patient has a genotype known to be associated with a disease that commonly causes the symptoms the patient exhibits. For example, if the genotyping methods of the invention show that the individual has a genotype associated with a particular disease and further that the genotype is associated with poor recovery (e.g., a mutant homozygote), the physician can counsel the client regarding the likely effectiveness of aggressive treatment options and the option of simply foregoing such treatments, especially if the disease is quite advanced. On the other hand, if the genotype is associated with good recovery, the physician can describe a range of treatment options varying from simply monitoring the disease to see if the condition worsens or more aggressive measures to ensure that the disease is attacked before it gets worse.

The methods of the present invention are also valuable for assessing the actual risk of an individual known to be susceptible to acquiring a disease (e.g., an individual coming from a family that has a history of suffering from a disease). By determining whether the individual is a mutant homozygote for the SNP associated with the disease or a heterozygote, a physician can more accurately assess and counsel the patient regarding the likelihood that the patient will begin suffering from disease, factors involved in triggering the disease and the pros and cons regarding different treatment alternatives.

Similarly, certain methods of the invention can also be used to identify individuals at risk for disease, even though they have no symptoms of disease or no known susceptibilities to disease. An individual in this category would generally have no disease symptoms and have no family history of disease. In such cases, the methods of the present invention can be used as a useful preventive screening tool. Using the methods of the present invention, a number of selected SNP sites known to be associated with certain diseases can be interrogated to identify the genotype of the individual at those sites. If a particular genotype were identified that was known to be associated with a particular disease, then a physician could advise the individual regarding the likelihood that the disease would manifest itself and the range of treatment options available.

C. Examples of Diseases that can be Monitored

A large number of diseases have been shown to be correlated with particular allelic forms of SNPs. A large number of such SNPs are listed in WO 93/02216 and by Cooper et al. (*Hum. Genet.* 85:55–74 (1990)). Specific examples of diseases associated with SNPs include: sickle cell anemia and β-thalassemias (mutation in β-globin gene; Antonarakis, *New Eng. J. Med.*, 320:153–163 (1989)), cystic fibrosis (mutation in cystic fibrosis transmembrane receptor (CFTR); see Kerem, et al., *Science* 245:1073–1080 (1989)), hyperlipoproteinemia (mutation in apolipoprotein E gene; see Mahley, *Science* 240:622–630 (1988)), a wide variety of autoimmune diseases (mutations in human major histocompatibility complex; see Thomson, *Ann. Rev. Genet.*, 22:31–50 (1988); Morel et al., *Proc. Nat. Acad. Sci. USA*, 85:8111–8115 (1988); and Scharf, et al., *Proc. Nat. Acad. Sci. USA* 85:3504–3508 (1988)) and the formation of oncogenes (mutations to the human ras-gene family; see, e.g., Bos et al., *Nature* 315:726–730 (1985); Farr et al., *Proc. Natl. Acad. Sci. USA* 85:1629–1633 (1988); and Neri, et al., *Proc. Natl. Acad. Sci. USA* 85:9268–9272 (1988)). Other genes containing SNPs associated with disease include genes encoding for angiotensinogen, angiotensin converting enzyme, cholesterol ester transfer protein, dopamine receptors, serotonin receptors, and HIV reverse transcriptase (RT). Mutations in P53 and cytochrome P450 genes are also associated with various diseases.

D. Other Uses

The methods described herein can also be used to identify point mutations in microorganisms that could potentially cause altered pathogenicity or resistance to certain therapeutics. The methods can also be used to identify cells and strains having a desired genetic constitution for use in various biotechnology applications.

The methods described herein can also detect the presence of somatic mutations that can result in various diseases, including cancer for example.

With knowledge gained from the genotyping capabilities of the methods described herein, clinicians can conduct prenatal testing using cells obtained from a fetus to check for a variety of inheritable diseases, such as those diseases associated with the SNPs listed above. The methods can also be used to identify carriers of mutant alleles. Such information can be of use by a couple prior to conception as they evaluate the risks of having a child with certain birth defects or inheritable diseases.

Methods of the invention may also be utilized in various identification applications, such as in the field of forensic medicine or paternal testing. In the case of forensic analysis, polymorphisms in specific genes can be determined in, for example, blood or semen obtained from a crime scene to indicate whether a particular suspect was involved in the crime. In like manner, polymorphism analysis may be utilized in paternity disputes to aid in determining whether a particular individual is the father of a certain child.

In another application, certain methods of the invention are used in blood typing or tissue classification. Tissue classifications, for example, can be determined by identifying polymorphisms specific for a particular individual.

X. Kits

The invention also provides kits for the detection of a variant site in a specific target nucleic acid. The kit generally includes: (a) a deoxynucleotide analog which, when incorporated into an extension product, is resistant to digestion by a 5'-3' exonuclease, (b) a 5'-3' exonuclease, and (c) an enzyme that digests single-stranded DNA. Some kits further include a primer that is complementary to a strand of a target nucleic acid of interest and binds adjacent to (but does not overlap) the variant site. The kit may also include another primer that is complementary to a segment of a second strand of the target nucleic acid; this primer also includes a nucleotide derivative that is resistant to digestion by a 5'-3' exonuclease. The nucleotide derivative included within the primer can include any of those described above. The primers in many instances will be for sequences associated with polymorphic genes known to be associated with diseases such as those set forth above. When the two primers have bound to their respective strands, they flank the variant site. The different types of deoxynucleotide analog that can be incorporated into the extension product and the different types of 5'-3' and single-stranded nucleases that can be utilized in the kit are as described above.

The kits may also include a variety of other components such as buffers, polymerases and dNTPs for conducting the amplification reactions, and instructions for performing the analysis. The kits may further include electrophoretic components to size separate the fragments that are formed during the analysis.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

What is claimed is:

1. A method for analyzing a variant site in a target nucleic acid, comprising:
   (a) amplifying said target nucleic acid by
      (i) providing a first and second primer, said first primer being complementary to a segment of a first strand of said target nucleic acid, the 3' end of said first primer being adjacent to but not overlapping said variant site, said second primer being complementary to a segment of a second strand of said target nucleic acid and including a nucleotide derivative resistant to digestion by a 5'-3' exonuclease, said first and second primer flanking said variant site, wherein said variant site is the site at which a first or second base is located; and
      (ii) conducting template dependent extension of said first and second primers in the presence of four deoxynucleoside triphosphates (dATP, dTTP, dGTP and dCTP), wherein one of said deoxynucleoside triphosphates is an analog of a natural deoxynucleotide which is resistant to digestion by said 5'-3' exonuclease, said deoxynucleotide analog selected to be the complement of said first or second base at said variant site in said second strand, and wherein said target nucleic acid serves as a template such that an amplified double-stranded product is generated;
   (b) digesting said double-stranded product with said 5'-3' exonuclease to form a digested product having a single-stranded segment;
   (c) removing said single-stranded segment with an enzyme that digests single-stranded DNA to produce a blunt end fragment; and
   (d) determining the size of said blunt end fragment as an indicator of whether said variant site includes said first or second base.

2. The method according to claim 1, wherein said 3' end of said first primer extends to and hybridizes with the base immediately 5' to said variant site.

3. The method according to claim 1, wherein said nucleotide derivative is located at the 5' end of said second primer.

4. The method according to claim 1, wherein the 3' end of said first primer and the 3' end of said second primer are separated by 5 to 1000 bases when both primers are hybridized to their respective strands.

5. The method according to claim 1, wherein said deoxynucleotide analog is selected from the group consisting of a thiol base, an unphosphorylated base, and a boronated analog.

6. The method according to claim 5, wherein said deoxynucleotide analog is a thiol base.

7. The method according to claim 1, wherein said nucleotide derivative is selected from the group consisting of a thiol base, a phosphorylated base, and a boronated analog.

8. The method according to claim 7, wherein said nucleotide derivative is a thiol base.

9. The method according to claim 1, wherein said 5'-3' exonuclease is selected from the group consisting of phage T7 gene 6 exonuclease and lambda exonuclease.

10. The method according to claim 1, wherein said enzyme that digests single-stranded DNA is selected from the group consisting of mung bean nuclease and S1 nuclease.

11. The method according to claim 1, wherein said determining step comprises determining the size of a strand of said blunt end fragment by mass spectroscopy.

12. The method according to claim 1, wherein said determining step comprises determining the size of at least one strand of said blunt end fragment by electrophoresis.

13. The method according to claim 12, wherein said determining step comprises analyzing said blunt end fragment by micro-channel electrophoresis.

14. The method according to claim 1, wherein said second primer includes a label.

15. The method according to claim 14, wherein said label is selected from the group consisting of a fluorophore, a chromophore, a radioisotope, a magnetic particle, and a mass label.

16. The method according to claim 15, wherein said label is a fluorescent label.

17. The method according to claim 16, wherein said fluorescent label is selected from the group consisting of fluorescein and fluorescein derivatives, rhodamine and rhodamine derivatives, cyanine and cyanine derivatives, bodipy and naphthylamine and naphythylamine derivatives.

18. The method according to claim 17, wherein said fluorescent label is selected from the group consisting of FAM, TET, JOE, TAMRA, R110, R6G and ROX.

19. The method according to claim 1, wherein said label is attached to the nucleotide located at the 5' end of said second primer.

20. The method according to claim 1, wherein said target nucleic acid is selected from the group consisting of the gene for cystic fibrosis transmembrane receptor, P53, a cytochrome P450, angiotensinogen, angiotensin converting enzyme, apolipoprotein E, cholesterol ester transfer protein, a dopamine receptor, a serotonin receptor and HIV RT, or fragments thereof which contain said variant site.

21. The method according to claim 14, wherein said determining step comprises denaturing said blunt end fragment to produce a labeled single strand, separating said labeled single strand by gel electrophoresis, and detecting said labeled single strand.

22. The method according to claim 1, wherein said amplifying step, said digesting step, said removing step and said determining step are all performed using a single integrated device.

23. The method according to claim 1, wherein said determining step includes checking for the presence of two different sized fragments, the presence of two different sized fragments being indicative of a heterozygous condition, and the presence of a single sized fragment being indicative of a homozygous condition.

24. The method according to claim 1, wherein
    (a) said 3' end of said first primer extends to and hybridizes with the base immediately 5' to the variant site;
    (b) said 3' end of said first primer and the 3' end of said second primer are separated by 5 to 1000 bases once both primers are hybridized to their respective strands;
    (c) said nucleotide derivative and said deoxynucleotide analog are thiol bases;
    (d) said 5'-3' exonuclease is selected from the group consisting of phage T7 gene 6 exonuclease and lambda exonuclease;
    (e) said enzyme that digests single-stranded DNA is selected from the group consisting of mung bean nuclease and S1 nuclease;
    (f) said second primer includes a fluorescent label; and
    (g) said determining step comprises denaturing said blunt end fragment to produce a labeled single-stranded product, separating said labeled single-stranded product by gel electrophoresis, and detecting said labeled single-stranded product.

25. A method for analyzing a first and second variant site in a first and second target nucleic acid, respectively, said method comprising:
    (a) amplifying said first and second target nucleic acid by
        (i) providing a first upstream and downstream primer pair, said first upstream primer being complementary to a segment of a first strand of said first target nucleic acid, the 3' end of said first upstream primer being adjacent to but not overlapping said first variant site, said first downstream primer being complementary to a segment of a second strand of said first target nucleic acid and including a nucleotide derivative resistant to digestion by a 5'-3' exonuclease, said first upstream and downstream primer flanking said first variant site, wherein said first variant site is the site at which a first or a second base is located;
        (ii) providing a second upstream and downstream primer pair, said second upstream primer being complementary to a segment of a first strand of said second target nucleic acid, the 3' end of said second upstream primer being adjacent to but not overlapping said second variant site, said second downstream primer being complementary to a segment of a second strand of said second target nucleic acid and including a nucleotide derivative resistant to digestion by a 5'-3' exonuclease, said second upstream and downstream primer flanking said second variant site, wherein said second variant site includes said first or said second base;
        (iii) conducting template dependent extension of said first and second primer pairs in the presence of four deoxynucleoside triphosphates (dATP, dTTP, dGTP and dCTP), wherein one of said deoxynucleoside triphosphates is an analog of a natural deoxynucleotide which is resistant to digestion by said 5'-3' exonuclease, said deoxynucleotide analog selected to be the complement of said first or second base at said first and second variant site in said second strand of said first and second target nucleic acid, and wherein said first and second target nucleic acid each serve as a template such that an amplified double-stranded product is generated from each of said first and second primer pair, thus generating a plurality of double-stranded products;
    (b) digesting said plurality of double-stranded products with said 5'-3' exonuclease to form a plurality of digested products each having a single-stranded segment;
    (c) removing single-stranded segments from said plurality of digested products with an enzyme that digests single-stranded DNA to produce a plurality of blunt end fragments; and
    (d) determining the size of said plurality of blunt end fragments to determine whether said first and second variant sites include said first or second base.

26. The method according to claim 25, wherein said first downstream primer includes a first label and said second downstream primer includes a second label.

27. The method according to claim 25, wherein said first and second label are selected from the group consisting of a fluorophore, a chromophore, a radioisotope, a magnetic label and a mass label.

28. The method according to claim 27, wherein said first label and said second label are the same.

29. The method according to claim 26, wherein said first label and said second label are different.

30. The method according to claim 29, wherein said first and second label are fluorescent labels.

31. The method according to claim 25, wherein said first and second target nucleic acid are a single nucleic acid and wherein said first and second variant site are different sites on said single nucleic acid.

32. The method according to claim 25, wherein said first and second target nucleic acid are different and wherein said first and second variant site are the same site on said first and second target nucleic acid.

33. A kit for analyzing a variant site in a target nucleic acid, comprising:
    (a) a deoxynucleotide analog for use in primer extension reactions which when incorporated into an extension product is resistant to digestion by a 5'-3' exonuclease;
    (b) said 5'-3' exonuclease; and
    (c) an enzyme that digests single-stranded DNA.

34. The kit according to claim 33, wherein said deoxynucleotide analog is selected from the group consisting of group consisting of a thiol base, a phosphorylated base and a boronated analog.

35. The kit according to claim 33, wherein said deoxynucleotide analog is a thiol base.

36. The kit according to claim 33, wherein said 5'-3' exonuclease is selected from the group consisting of phage T7 gene 6 exonuclease and lambda exonuclease.

37. The kit according to claim 33, wherein said enzyme that digests single-stranded DNA is selected from the group consisting of mung bean nuclease, and S1 nuclease.

38. The kit according to claim 33, further comprising:
(a) a first primer complementary to a segment of a first strand in said target nucleic acid such that the 3' end of said upstream primer is adjacent to but does not overlap said variant site; and
(b) a second primer complementary to a downstream segment of a second strand of said target nucleic acid and including a nucleotide derivative resistant to digestion by an exonuclease.

39. The kit according to claim 38, wherein said target nucleic is selected from the group consisting of the gene for cystic fibrosis transmembrane receptor, P53, P450, angiotensinogen, angiotensin converting enzyme, apolipoprotein E, cholesterol ester transfer protein, a dopamine receptor, a serotonin receptor and HIV RT, or fragments thereof which contain said variant site.

* * * * *

SEQUENCE LISTING

<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:primer 1

<400> SEQUENCE: 1
tccagctacg ctcactcagc                                                    20

<210> SEQ ID NO 2
<211> LENGTH: 96
<212> TYPE: DNA
<213> ORGANISM: Artificial Sequence
<220> FEATURE:
<223> OTHER INFORMATION: Description of Artificial Sequence:target

<400> SEQUENCE: 2
tacgtccagc tacgctcact cagcracgtc gttagcatta cgagccagct acacgatcct        60
acatcctgcc gtcgttagct acgagctaga tacgat                                  96

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:primer 2

<400> SEQUENCE: 3
cgtatctagc tcgtagctaa                                                    20

<210> SEQ ID NO 4
<211> LENGTH: 96
<212> TYPE: DNA
<213> ORGANISM: Artificial Sequence
<220> FEATURE:
<223> OTHER INFORMATION: Description of Artificial Sequence:A allele
      target

<400> SEQUENCE: 4
tacgtccagc tacgctcact cagcaacgtc gttagcatta cgagccagct acacgatcct        60
acatcctgcc gtcgttagct acgagctaga tacgat                                  96

<210> SEQ ID NO 5
<211> LENGTH: 96
<212> TYPE: DNA
<213> ORGANISM: Artificial Sequence
<220> FEATURE:
<223> OTHER INFORMATION: Description of Artificial Sequence:G allele
      target

<400> SEQUENCE: 5
tacgtccagc tacgctcact cagcgacgtc gttagcatta cgagccagct acacgatcct        60
acatcctgcc gtcgttagct acgagctaga tacgat                                  96

<210> SEQ ID NO 6
<211> LENGTH: 90
<212> TYPE: DNA
<213> ORGANISM: Artificial Sequence
<220> FEATURE:
<223> OTHER INFORMATION: Description of Artificial Sequence:A allele 90 bp PCR product

<400> SEQUENCE: 6
tccagctacg ctcactcagc aacgtcgtta gcattacgag ccagctacac gatcctacat    60
cctgccgtcg ttagctacga gctagatacg                                    90

<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence:G allele 90
      bp PCR product

<400> SEQUENCE: 7
tccagctacg ctcactcagc gacgtcgtta gcattacgag ccagctacac gatcctacat    60
cctgccgtcg ttagctacga gctagatacg                                    90

<210> SEQ ID NO 8
<211> LENGTH: 70
<212> TYPE: DNA
<213> ORGANISM: Artificial Sequence
<220> FEATURE:
<223> OTHER INFORMATION: Description of Artificial Sequence:A allele
      exonuclease digestion product and single stranded
      digestion product

<400> SEQUENCE: 8
aacgtcgtta gcattacgag ccagctacac gatcctacat cctgccgtcg ttagctacga    60
gctagatacg                                                          70

<210> SEQ ID NO 9
<211> LENGTH: 90
<212> TYPE: DNA
<213> ORGANISM: Artificial Sequence
<220> FEATURE:
<223> OTHER INFORMATION: Description of Artificial Sequence:A allele
      exonuclease digestion product

<400> SEQUENCE: 9
cgtatctagc tcgtagctaa cgacggcagg atgtaggatc gtgtagctgg ctcgtaatgc    60
taacgacgtt gctgagtgag cgtagctgga                                    90

<210> SEQ ID NO 10
<211> LENGTH: 69
<212> TYPE: DNA
<213> ORGANISM: Artificial Sequence
<220> FEATURE:
<223> OTHER INFORMATION: Description of Artificial Sequence:G allele
      exonuclease digestion product and single stranded
      digestion product

<400> SEQUENCE: 10
acgtcgttag cattacgagc cagctacacg atcctacatc ctgccgtcgt tagctacgag    60
ctagatacg                                                           69

<210> SEQ ID NO 11
<211> LENGTH: 90
<212> TYPE: DNA
<213> ORGANISM: Artificial Sequence
<220> FEATURE:
<223> OTHER INFORMATION: Description of Artificial Sequence:G allele
      exonuclease digestion product

<400> SEQUENCE: 11
cgtatctagc tcgtagctaa cgacggcagg atgtaggatc gtgtagctgg ctcgtaatgc    60
taacgacgtc gctgagtgag cgtagctgga                                    90

<210> SEQ ID NO 12
<211> LENGTH: 67
<212> TYPE: DNA
<213> ORGANISM: Artificial Sequence
<220> FEATURE:
<223> OTHER INFORMATION: Description of Artificial Sequence:A allele
      exonuclease digestion product and single stranded
      digestion product

<400> SEQUENCE: 12
gtcgttagca ttacgagcca gctacacgat cctacatcct gccgtcgtta gctacgagct    60
agatacg                                                             67

<210> SEQ ID NO 13
<211> LENGTH: 70
<212> TYPE: DNA
<213> ORGANISM: Artificial Sequence
<220> FEATURE:
<223> OTHER INFORMATION: Description of Artificial Sequence:G allele
      exonuclease digestion product and single stranded
      digestion product

<400> SEQUENCE: 13
gacgtcgtta gcattacgag ccagctacac gatcctacat cctgccgtcg ttagctacga    60
gctagatacg                                                          70

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:
      second/template strand

<400> SEQUENCE: 14
tcgatgcgag tgagtcgttg c                                             21

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:variant site
      primer

<400> SEQUENCE: 15
agctacgctc actca                                                    15

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence:unsuitable
      sequence for variant site primer

<400> SEQUENCE: 16
agctacgctc actc                                                     14

<210> SEQ ID NO 17

```
-continued

<211> LENGTH: 21
<212> TYPE: DNA
<213> ORGANISM: Artificial Sequence
<220> FEATURE:
<223> OTHER INFORMATION: Description of Artificial Sequence:
      second/template strand

<400> SEQUENCE: 17
tcgatgcgag tgagtcggtg c                                              21
```